United States Patent [19]

Dietz

[11] Patent Number: 4,537,074
[45] Date of Patent: Aug. 27, 1985

[54] ANNULAR ARRAY ULTRASONIC TRANSDUCERS

[75] Inventor: Dennis R. Dietz, Littleton, Colo.

[73] Assignee: Technicare Corporation, Solon, Ohio

[21] Appl. No.: 530,687

[22] Filed: Sep. 12, 1983

[51] Int. Cl.³ ............................................. G01N 29/00
[52] U.S. Cl. ......................................... 73/625; 73/628
[58] Field of Search ................... 73/625, 626, 628, 641, 73/620; 310/334, 335, 336; 367/103, 105, 155; 128/660

[56] References Cited

U.S. PATENT DOCUMENTS

| | | | |
|---|---|---|---|
| 3,086,195 | 4/1963 | Halliday | 73/640 |
| 4,012,952 | 3/1977 | Dory | 73/612 |
| 4,058,003 | 11/1977 | Macovski | 73/620 |
| 4,137,777 | 2/1979 | Haverl et al. | 73/626 |
| 4,138,895 | 2/1979 | Mezrich | 73/626 |
| 4,155,259 | 5/1979 | Engeler | 73/626 |
| 4,241,611 | 12/1980 | Specht et al. | 73/626 |
| 4,276,779 | 7/1981 | Davis, Jr. | 73/626 |
| 4,395,652 | 7/1983 | Nakanishi et al. | 73/625 |
| 4,398,539 | 8/1983 | Proudian | 73/626 |
| 4,487,073 | 12/1984 | Sumino | 73/625 |

OTHER PUBLICATIONS

M. Ueda et al., "Dynamic Focusing Ultrasonic Transducers Using Analog-Switch Phase Shifters", Elec. and Comm. in Japan, vol. 58-A, No. 12, pp. 1-8, Dec. 1976.
D. R. Dietz et al., "Expanding-Aperture Annular Array", Ultrasonic Imaging, pp. 56-75, vol. 1, No. 1, Jan 1979.

Primary Examiner—Stephen A. Kreitman
Attorney, Agent, or Firm—W. Brinton Yorks, Jr.

[57] ABSTRACT

An annular array ultrasonic transducer is provided which comprises a plurality of concentric rings of piezoelectric material having widths chosen for operation at different depths of focus. The total aperture of the transducer is divided into a plurality of contiguous focal depths. In the near field only the inner element or elements are activated, and rings of increasing radius are added as the depth of focus is increased. The widths of the rings are chosen to keep phase errors across each ring within acceptable limits over the depth of field for which they are energized. The transition depths at which the aperture is changed are chosen to allow rings of manufacturable widths to be employed while maintaining aperture transitions which prevent banding in the ultrasonic image.

10 Claims, 7 Drawing Figures

ANNULAR ARRAY ULTRASONIC TRANSDUCERS

This invention relates to annular array transducers for ultrasonic diagnostic systems and, in particular, to annular array transducers having elements optimized for desired focal distances and exhibiting smooth transitions between successive focal ranges.

The use of multi-element transducers for ultrasound systems advantageously permits the characteristics of the transducer to be varied electronically. By using different element combinations, the aperture and focal depth characteristics can be controllably varied during use, permitting the collection of highly resolved information over a wide range of tissue depths. Two types of multi-element transducers are the linear array, and the annular array such as that shown in U.S. Pat. No. 4,138,895 (Mezrich). The Mezrich annular array comprises a flat plate having a central disc-shaped element and an outer concentric ring-shaped element. For near field imaging only the central element is used, and for far field imaging the two elements are used together. The elements, together or independently, are mechanically focused at infinity due to the flat plate design. The use of one or two elements changes the size, and hence the amount of energy which may be transmitted and collected by the transducer, much as squinting and widely opening the eyelids adjusts the amount of light admitted to the eyes.

A different type of annular array is the curved surface annular array, whereby the elements are formed as parts of a spherical surface. With the central disc element at the pole of the concave surface of the sphere and concentric ring elements surrounding it, the spherical surface annular array is mechanically focused at the geometric center of the sphere. This advantageously permits the collection of highly resolved information in the vicinity of the geometric focal point, but requires sophisticated techniques when forcing the transducer to focus at other than its natural focal point.

Several varieties of annular arrays have been developed. Typical of one kind is the concave annular array shown in U.S. Pat. No. 4,155,259 (Engeler), in which the piezoelectric surface is divided into rings of increasing radii but constant width. This array is relatively easy to manufacture, since the rings are all the same width, but presents complications at the electronic interface. The impedance of each ring is a function of its area, and the area of each ring differs from that of all others by a factor proportional to the square of the radius of the particular ring. Thus, the rings all present different impedances to the transmit/receive electronics.

Another kind of concave annular array is the Fresnel plate array, in which all rings exhibit the same area. A typical Fresnel plate transducer is illustrated in FIG. 7b of the above-referenced Engeler patent. While the Fresnel plate transducer alleviates the impedance differential problem by reason of the equal areas of the rings, it also presents fabrication difficulties. Equal ring areas mean that rings of increasing radial distance from the center of the transducer must have correspondingly smaller ring widths. The outer rings of the transducer become thinner and thinner, which makes them fragile, difficult to fabricate, and difficult to couple to conductors.

Other considerations should go into the design of all annular array transducers, such as phase errors across the face of the transducer. At points other than the geometric focus the distances from the transducer axis to different points on the transducer surface are different. These differences, and their effects on signal phase, will affect transducer performance. Beam width, or aperture, is a second consideration. The ultrasonic beam will naturally diverge at increasing distances from the transducer, but close to the transducer the size of the beam is governed by the physical size of the energized transducer elements. It is desirable on one hand to have a large active transducer for the transmission and reception of significant ultrasonic energy, but on the other hand it is desirable to maintain a small aperture for good image resolution. Finally, one should consider the step changes in the aperture as different rings are activated and deactivated. If the aperture changes are not relatively smooth, transitional distortions will be apparent in the ultrasonic image where rings are switched in and out at different focal depths. These distortions generally manifest themselves as banding in the image as the sensitivity of the transducer experiences step changes between different focal regions.

In accordance with the principles of the present invention, a concave annular array transducer is provided having piezoelectric rings of different radii designed for operation at different depths of focus. The total aperture of the transducer is divided into a plurality of contiguous focal depths. In the near field, only the inner element or elements are used to focus the transmitted and received ultrasound. The widths of these elements are chosen to keep phase errors across them within acceptable limits. As the depth of field is increased, piezoelectric rings of increasing radii are energized in combination with those already energized at less distant depths. The widths of these rings are also determined in accordance with phase criteria, and the transition depths at which the aperture is changed is chosen to allow the ring widths to be within the limits of acceptable manufacturing tolerances. The aperture is chosen in accordance with the focal depth and ring radii so that aperture transitions are kept below the level of incremental change at which banding would appear in the ultrasonic image.

Figure 1:
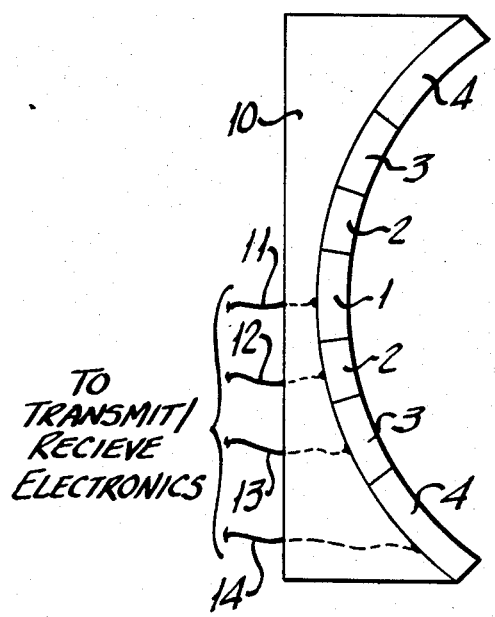
FIG. 1 illustrates a cross-sectional view of a concave annular array transducer constructed in accordance with the principles of the present invention.
Figure 2:
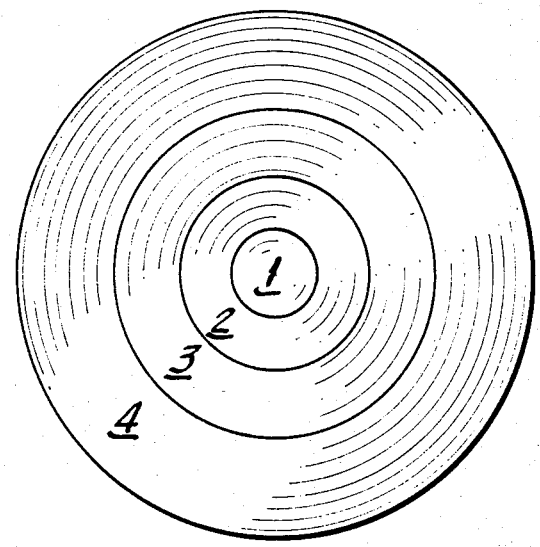
FIG. 2 illustrates a planar view of the face of an annular array transducer constructed in accordance with the principles of the present invention.

Referring concurrently to FIGS. 1 and 2, an annular array transducer constructed in accordance with the principles of the present invention is shown. The transducer comprises a curved surface of piezoelectric material, such as lead zirconate titanate which has been sliced into rings 1–4, as shown in FIG. 2, which illustrates the face of the transducer. In the cross-sectional view of FIG. 1, the transducer is shown with a backing 10 comprised of a sound absorbing backing material which may be loaded with a filler to damp oscillations from the rear of the transducer. Wires 11, 12, 13 and 14 are connected to respective rings 1, 2, 3 and 4 to conduct electrical signals to and from the rings.

The dimensions of the rings and their number are determined by the intended frequency of operation of the transducer, the depth of field over which the transducer is expected to operate, and the maximum acceptable phase error. Also, the fabrication process of the ceramic transducer material should be taken into consideration. When these factors are considered the dimensions of the array and the individual ring elements may be optimized for operation of specific ring combinations over different depth of focus ranges.

Figure 3:
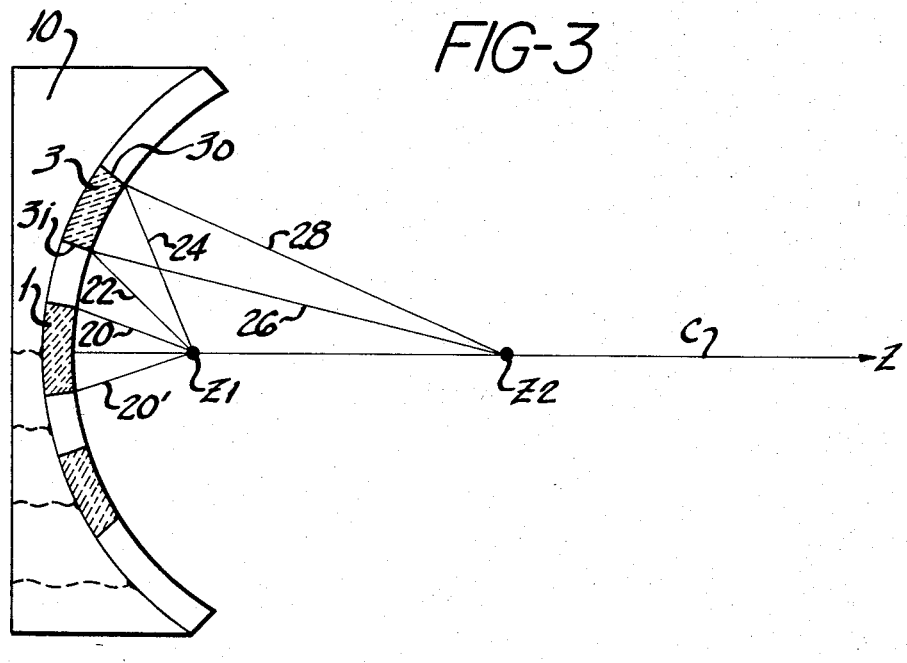
FIG. 3 illustrates range and element phase characteristics of the transducer of FIG. 1.

What is meant by acceptable phase error may be understood by referring to FIG. 3. FIG. 3 illustrates the transducer of FIG. 1, with emphasis on the central disc 1 and the outer ring element 3. A center line C emanates from the center of the array into the field of operation in the Z direction.

Ideally, an ultrasonic echo signal returning from a point in the region under examination should reach every point on the face of the transducer at the same instant in time. If an echo signal reaches one point on a transducer element at one time and different point on the element at a later time, the received signal will have two different phases at the two points of reception. The phase error developed thereby can lead to inaccuracies in the ultrasonic image when signals from different elements are combined for image formation and phase cancellation occurs.

Phase error analysis is done with respect to two points on the center line C in FIG. 3. The phase error is a function of signal transmit time, which may also be expressed in terms of the signal path length. For instance, the path lengths from the near field point Z1 to the outer edges of the central disc 1, 20 and 20', are of equal length by reason of the symmetry of the central disc. Thus a signal travelling from point Z1 to the central disc 1 will reach the edges of the disc at the same instant in time. However, a signal from point Z1 will travel a shorter path to reach the center of the disc by reason of the disc curvature. There will thus be a phase error radially from the center to the edge of disc 1 for signals received by the disc from point Z1.

A different situation applies in the case of the outer ring 3. The distance 22 from near field point Z1 to the inner edge 3i of element 3 is shorter than the distance 24 from Z1 to the outer edge 3o of the ring. There will thus be a phase differential of the received signal across the width of the ring 3. The phase error could only be eliminated if the ring had a width of zero; hence it is necessary to consider what magnitude of phase error may be tolerated, and how narrow a ring width may be reliably produced by the ceramic fabrication technology employed.

At a far field point Z2, however, a different phase error condition exists. When Z2 is less than the distance of the geometric focal point of the curvature of the face of the array, the path length 28 to the outer edge 3o is only slightly greater than the path length to the inner edge 3i. At the exact geometric focal point the distances would be identical, and beyond the geometric focal point the length relationship reverses. The relatively smaller path length differential at the far field point Z2 means that signals from that point will be received with a smaller phase error across the width of the ring than is the case from nearer field points. The implication of this relationship makes it desirable to use rings of increasing radii only for far field signal detection, as the phase errors experienced may then be within acceptable limits. A second realization is that outer rings of relatively sizable width, which are easier to fabricate, may be used for far field imaging.

Figure 1A:
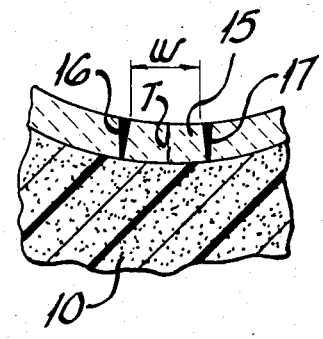
FIG. 1a illustrates a cross-sectional view of an outer ring of a Fresnel type annular array transducer.

When the outer ring widths of the transducer exhibit ever decreasing ring widths, as is the case for Fresnel plate transducers, they become thinner and more fragile, and their ultrasonic properties can change. FIG. 1a shows a thin ring 15, for which the ring width w is approaching the ring thickness T. The ring 15 is defined by grooves 16 and 17 in the piezoelectric material. During ultrasonic transmission the element will resonate so that ultrasonic waves will emanate from the largest dimensional surface of the transducer, which should be the outer curved face. But when w approaches the dimension T of the thickness, the ring approaches the state where resonance transmits energy from the sides of the ring into grooves 16 and 17 and into the surrounding rings. The altered transmissive characteristic of the thin ring thereby results in a transducer of poor efficiency.

The dimensions of the annular array transducer of the present invention are determined by first deciding upon the field depth over which the transducer is intended to operate. The depth of field for the embodiment of FIGS. 1 and 3 was fixed at 130 mm, ranging from a minimum depth along the Z axis of FIG. 3 of 40 mm (Z min) to a maximum depth of 170 mm (Z max).

The curvature of the transducer was then fixed by choosing a geometric focal point along the Z axis. A maximum acceptable phase error of $\pi/1.1(163°)$ was decided upon. The geometric focal point was then determined so that the phase error across the minimal transducer aperture is the same magnitude and of opposite sign at Z min and Z max, using the relationship $$\phi_e = \frac{\pi}{\lambda} \frac{r^2}{2}\left(\frac{1}{Z} - \frac{1}{G}\right)$$

where r is the radius of the transducer during operation at Z min, G is the geometric focal point, $\lambda$ is the wavelength of the ultrasonic frequency, and Z is either Z min or Z max. The transducer radius r for operation at Z min is chosen by deciding upon an aperture value at Z min which gives a desired resolution at that point. The resolution is a function of the F number, which is calculated by dividing the focal distance Z by the transducer diameter, 2r. The desired Z min value of 40 mm and a selected F number are then used in this equation to solve for r. This r value is inserted into the above equation, which is solved simultaneously using Z min and Z max for opposite signs and the same magnitude $\phi_e$. The geometric focal point G is then determined from these equations, using a radius r for the desired resolution (F number) at Z min. For a 5MHz frequency of operation the geometric focal point for the desired depth of field of a 19 mm diameter transducer was found to be 93 mm. The 93 mm value is the radius of curvature of the spherical transducer face.

A minimal acceptable ring width was then determined in light of the fabrication process used to form the transducer rings. It was decided that the transducer rings should be greater than 0.9 mm in width, and a minimal width of 1.4 mm was selected.

Figure 4:
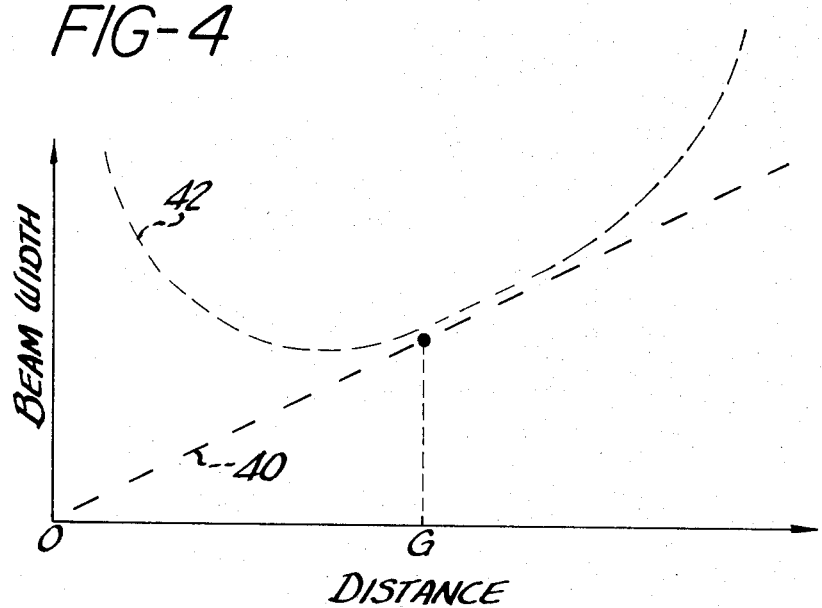
FIGS. 4 and 5 illustrate aperture characteristics of annular array transducers.

The width of the central element is then determined. The desired beam width should now be considered, since beam width will determine the focal characteristics or aperture of the transducer. FIG. 4 shows a graphical representation of the beam width as a function of distance or depth of field. Broken line 42 represents the beam width of a fixed focus (single element) spherical faced transducer referenced to the theoretical diffraction limited reference line 40. At short distances the beam width is large, as it is there primarily a function of the transducer diameter. At increasing distances the beam converges as it approaches the geometric focal point G of the spherical surface. The beam is most highly converged as it tangentially approaches the theoretical reference line just before the geometric focal point G, whereafter the beam diverges.

It is desirable to keep the beam as narrow as possible throughout the range of interest for good focal characteristics. FIG. 4 indicates that substantial improvement may be made in the near field through use of a small diameter transducer in the near field. As focal depth increases the annular array transducer successively activates the outer rings to optimize the transducer aperture for different focal depth regions. But as the focal distance increases and more annular rings are added to the operational transducer the aperture is changed in a step-wise manner each time an additional ring is added. This is expressed by the F number of the aperture, which is calculated as $$F\# = \frac{\text{focal distance}}{\text{diameter}} = \frac{Z}{D}$$

The F number steps should be minimized to prevent banding in the ultrasonic images at transitions from one ring combination to the next. While it is desirable to keep the central disc small so as to provide a narrow near field beam, consideration must be given to maintaining F number increments below the level at which banding occurs as additional rings are activated, without the necessity of adding a great many thin rings to the active transducer for maintenance of a smooth transitional characteristic.

While only the central disc 1 may be activated for near field focusing, it was found that the use of both a central disc 1 and the next annular ring 2 in the near field provided better resolution. The width of the central disc 1 and first ring 2 was then calculated so that the phase error across the disc and ring together did not exceed the desired phase criteria of $\pi/1.1$. The formula used was $$\phi_e = \frac{\pi}{\lambda} \frac{r_o^2}{2}\left(\frac{1}{Z} - \frac{1}{G}\right)$$

The calculations were performed using the distance Z min for the Z term and the desired phase criteria of $\pi/1.1$ for $\phi_e$. This fixed the outer radius $r_o$ of the first ring 2 at 5.6 mm. A ring width of 1.5 mm was then chosen for ring 2 and an interelement spacing of 0.3 mm was used for the fabrication technology employed. This resulted in a radius of 3.8 mm for the central disc 1.

The central disc 1 and ring 2 operate over a range from Z min to a point more distant along the Z axis at which a further ring of at least 1.4 mm can be added without causing a visible aperture transition (banding resulting from an F number change) in the image. Since F number changes of 50% are to be avoided to prevent banding, these considerations led to the decision to add the next ring 3 at a range Z of 48 mm. The width of the ring 3 was then calculated from the phase criteria $\pi/1.1$ using the following formula:

$$\phi_e = \frac{\pi}{\lambda} \frac{(r_o^2 - r_i^2)}{2}\left(\frac{1}{Z} - \frac{1}{G}\right)$$

with $r_o$ being the outer radius of ring 3 and $r_i$ being its inner radius. Z is set to 48 mm, the minimum distance at which disc 1 and rings 2 and 3 are used together. The $r_i$ term is known to be the outer radius of ring 2, 5.6 mm, plus the interelement spacing of 0.3 mm, giving an $r_i$ term equal to 5.9 mm. The formula is then solved for $r_o$, and gives a ring 3 width value of 1.4 mm.

The F number of the combination of rings 1, 2, and 3 was then plotted to determine where a further ring of at least 1.4 mm should be added without causing an F number transition in excess of 50%. These considerations dictated ending the second focal region at 60 mm. The phase error formula used for ring 3 was employed to determine the width of the next ring 4. The phase error from the inner edge to the outer edge of ring 4 at 60 mm was found to meet the desired phase criteria of $\pi/1.1$ for a ring 4 width of 1.9 mm. This ring width is advantageously larger than the widths of the previous two rings by reason of its employment in the vicinity of the geometric focus point and makes the outer ring less susceptible to breakage. With brittle ceramic material it is desirable to make the outer ring as wide as possible.

Figure 6:
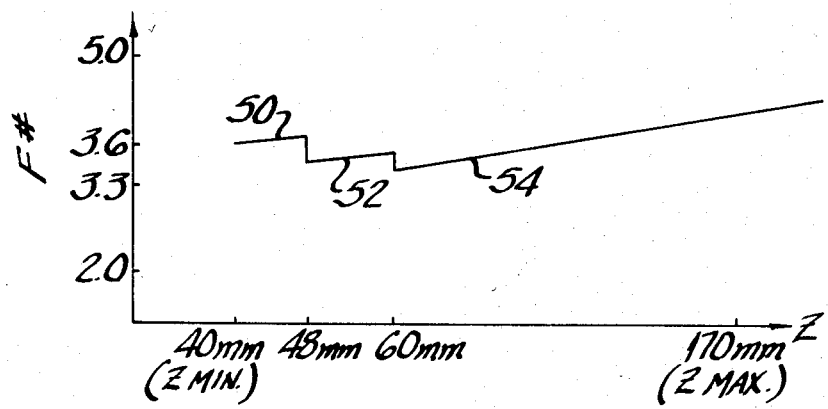
FIG. 6 illustrates aperture changes during operation of a multi-element annular array transducer constructed in accordance with the principles of the present invention.
Figure 5:
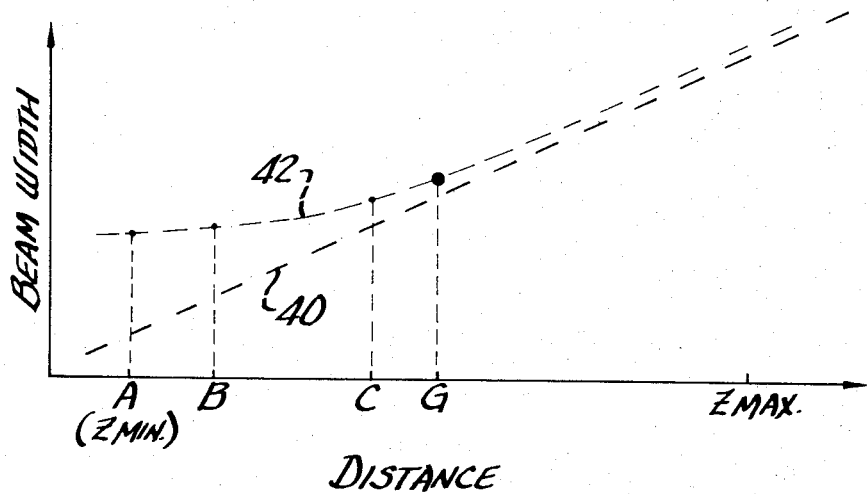

The beam characteristics of the annular array transducer having the above dimensions are illustrated by FIGS. 5 and 6. FIG. 5 shows a reasonably small near field beam width. In FIG. 5 the aperture is formed by central disc 1 and ring 2 between points A and B; by the central disc 1 and rings 2 and 3 between points B and C; and by the central disc and all three rings beyond point C.

FIG. 6 illustrates the F number aperture characteristics over the depth of field from Z min to Z max. The minimum F number is seen to be kept between 3.5 and 4.5 throughout the near field and into the far field. Beyond the 60 mm point the F number increases continuously, since all rings are activated and the aperture is then fixed at its maximum size. If the F number were allowed to increase to 6 or drop to 2 in the near field focal regions where the aperture is changed, the aperture changes would be severe, fluctuating by more than 50%. Banding in the displayed image would be evident as the transducer sensitivity experienced these sizable step changes, a problem which is not presented by the annular array transducer of the present invention. A conservative design approach would limit F number transitions to no more than 20% to 30% of the absolute value of the F number. Although the rings of different widths do not present identical impedances to the electronic circuits connected to the rings, the rings do present impedances which are all within an acceptable impedance range.

What is claimed is:

1. A selectable focus annular array ultrasonic transducer comprising a concave of piezoelectric material which is separated into a plurality of concentric rings including a central disc-shaped element and capable of being selectively focused over consecutive regions of a given depth of field by activating rings of increasing radii in combination with said disc-shaped element and rings activated in shorter field regions, if any, as the transducer is focused at increasing depths of field; each ring exhibiting a width selected in accordance with a predetermined phase criterion such that the received signal phase error across the ring width does not exceed a given signal phase change for signals received from the nearest field point at which the ring is initially activated.

2. The ultrasonic transducer of claim 1, wherein each ring combination used in said respective regions produces a beam of ultrasonic energy of a different aperture, said aperture exhibiting a transition in size at adjacent region boundaries which does not exceed 50% of the aperture size of the aperture of the near field region of said adjacent regions.

3. The ultrasonic transducer of claim 1, wherein said nearest field point is located on an axis extending normal to the center of the transducer; and wherein said given signal phase change is approximately $\pi/1.1$.

4. The ultrasonic transducer of claim 2, wherein said aperture exhibits an F number between 3 and 5 for near field regions and at least a portion of the region most distant from the transducer.

5. The ultrasonic transducer of claim 1, wherein the curvature of said concave surface provides said transducer with a geometric focal point locted in said given depth of field which provides the transducer with a phase change across the minimal transducer aperture at the opposite extremes of said depth of field of the same magnitude and opposite polarity.

6. The ultrasonic transducer of claim 5, wherein said geometric focal point is located in the region most distant from the transducer.

7. The ultrasonic transducer of claim 1, wherein the width of the ring of greatest radius is greater than the widths of the rings with radii intermediate the radius of said disc-shaped element and said ring of greatest radius.

8. The ultrasonic transducer of claim 7, wherein said disc-shaped element and the ring surrounding and adjacent to said disc-shaped element are activated in the nearest region of said given depth of field.

9. A selectable focus annular array ultrasonic transducer comprising a concave surface of piezoelectric material which is separated into a central disc region and a plurality of concentric rings surrounding said central disc and capable of being selectively focused over consecutive regions of a given depth of field by activating different ring combinations of increasing radii in regions of increasing depth of field; said rings each having a width exhibiting a phase change thereacross which does not exceed a given predetermined signal phase change for signals received from the nearest field for which they are activated; and at least one of said rings radially remote from said disc exhibiting a greater width than at least one of said rings which is radially less remote from said disc.

10. A selectable focus annular array ultrasonic transducer comprising a concave surface of piezoelectric material which is separated into a central disc region and a plurality of concentric rings surrounding said central disc, and capable of being selectively focused over consecutive regions of a given depth of field by activating different ring combinations of increasing radii in regions of increasing depth of field; said concave surface exhibiting a curvature which provides a geometric focal point such that the phase error for received signals across the transducer aperture is substantially the same magnitude but of opposite sign at approximately the minimal and maximal limits of said depth of field; said rings each exhibiting a width providing a phase error thereacross when activated which does not exceed $\pi/1.1$ degrees for a received ultrasonic signal.

* * * * *

UNITED STATES PATENT AND TRADEMARK OFFICE
CERTIFICATE OF CORRECTION

PATENT NO. : 4,537,074

DATED : August 27, 1985

INVENTOR(S) : Dennis R. Dietz

It is certified that error appears in the above-identified patent and that said Letters Patent is hereby corrected as shown below:

Column 6, line 67 - Insert the word --surface-- between the words "concave" and "of".

Signed and Sealed this

Fourth Day of November, 1986

[SEAL]

*Attest:*

DONALD J. QUIGG

*Attesting Officer*  *Commissioner of Patents and Trademarks*